(12) United States Patent
Li et al.

(10) Patent No.: US 7,785,793 B2
(45) Date of Patent: Aug. 31, 2010

(54) METHOD FOR ISOLATING AND MODIFYING DNA FROM BLOOD AND BODY FLUIDS

(76) Inventors: Weiwei Li, 338 38th St., Lindenhurst, NY (US) 11757; Jessica Li, 338 38th St., Lindenhurst, NY (US) 11757

( * ) Notice: Subject to any disclaimer, the term of this patent is extended or adjusted under 35 U.S.C. 154(b) by 0 days.

(21) Appl. No.: 12/287,480

(22) Filed: Oct. 9, 2008

(65) Prior Publication Data
US 2009/0042308 A1  Feb. 12, 2009

Related U.S. Application Data

(63) Continuation of application No. 11/703,983, filed on Feb. 8, 2007, now abandoned.

(51) Int. Cl.
  *C12Q 1/68* (2006.01)
(52) U.S. Cl. .......................................................... 435/6
(58) Field of Classification Search ...................... None
  See application file for complete search history.

(56) References Cited

OTHER PUBLICATIONS

Mizugaki et al. (Biol. Pharm. Bull. 1996 vol. 19, p. 1537-1540).*

* cited by examiner

*Primary Examiner*—Jacob Cheu

(57) ABSTRACT

This invention is related to a method and assay kit for rapidly quantifying global DNA methylation through immobilizing DNA by simple dry-capture on the plastic carrier followed by immunodetection of 5-methylcytosine structure that is the marker of DNA methylation.

3 Claims, 5 Drawing Sheets

METHOD FOR ISOLATING AND MODIFYING DNA FROM BLOOD AND BODY FLUIDS

This is a continuation of parent application Ser. No. 11/703,983 filed on Feb. 8 2007 and entitled "Method of rapidly quantifying global DNA methylation"

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

1. Field of the Invention

This invention is related to a method and assay kit for rapidly quantifying global DNA methylation through immobilizing DNA by simple dry-capture on the plastic carrier followed by immunodetection of 5-methylcytosine structure that is the marker of DNA methylation.

2. Description of the Related Art

DNA methylation is an epigenetic modification which is catalyzed by DNA cytosine-5-methyltransferases (DNMTs) and occurs at the 5-position (C5) of the cytosine ring, within CpG dinucleotides. DNA methylation is essential in regulating gene expression in nearly all biological processes including development, growth, and differentiation (Laird P W et al: Annu Rew. Genet, 1996; Reik W et al: Science, 2001; Robertson K D et al: Nature Rew. Genet, 2005). Alterations in DNA methylation have been demonstrated to cause the change in the gene expression. For example, hypermetlhylation leads to gene silencing or decreased gene expression while hypomethylation activates the genes or increases gene expression. Region-specific DNA methylation is mainly found in 5'-CpG-3'dinucleotides within the promoters or in the first exon of genes, which is an important pathway for the repression of gene transcription in diseased cells. Global DNA hypomethylation is likely caused by methyl-deficiency due to a variety of environmental influences, and has been proposed as a molecular marker in multiple biological processes such as cancer. It is well demonstrated that the decrease in global DNA methylation is one of the most important characteristics of cancer (Feinberg A P et al, Nature, 1983; Gama-Sosa M A et al, Nucleic Acids Res, 1983). Thus the determination of global methylation in cancer cells could provide very useful information for the detection and analysis of this disease. Many methods for the detection of global DNA methylation have been developed. These methods include: (1) high-performance liquid chromatography or thin-layer chromatography analysis (Breter H J et al: J chromatogr, 1976; Wagner I et. Al: Biochim Biophys Acta, 1981; Leonard S A et al: J chromatogr, 1993). In the analysis, DNA is digested into single nucleotides and total genomic 5-methylcytosine is quantified; (2) immunohistochemical staining in which tissue section is staining with anti-5-methylcytosine antibody to detect 5-methylcytosine positive cells (Hernandez-Blazquez F J et al: Gut, 2000; Piyaphilake C J et al: Dis Markers, 2005); (3) dot blot assay in which DNA is dot-blotted onto a nitrocellulose membrane followed by immunodetection of methylcytosine (Oakeley E. J et al: Proc. Natl. Acad. Sci. USA, 1997; Tao L et al: Toxic. Sci, 2005); (4) methyl accepting capacity or radiolabeled methyl incorporation (RMI) assay in which DNA is incubated with 3H—S-adenosylmethionine (3H—SAM) in the presence of methylase and RMI is inversely related to the degree of DNA methylation. (Wu J et al: Proc. Natl. Acad. Sci. USA, 1993; Belinsky S A et. al: Proc. Natl. Acad. Sci. USA, 1996); (5) analysis of repetitive DNA element methylation by PCR (Yang A S et al: Nucleic Acids Res, 2004). However these methods are labor intensive, time-consuming, or require large amounts of DNA (>250 ng) as the starting material for measurement, or rely on the use of expensive equipment and radioisotope reagents. These disadvantages lead to cost-ineffectiveness, low throughput and inconvenience for routine application in most health and medical institutions. Thus, there is a need for establishing a method to improve the detection of global DNA methylation.

BRIEF SUMMARY OF THE INVENTION

The present invention provides an improved method and kit which rapidly quantify global DNA methylation through immunodetection of 5-methylcytosine structure comprising the step of:
1) Isolation and purification of DNA from biological materials;
2) Coating of the plastic carrier with the nucleic acid binding substance;
3) Immobilization of DNA by dry-capture on the plastic carrier which is coated with the nucleic acid binding substance;
4) Detection of 5-methylcytosine structure contained in the DNA with the anti-5-methylcytosine specific antibody;
5) Detection of anti-5-methylcytosine antibody with the secondary antibody conjugated with label molecules;
6) Fluorescent or color development of antibody conjugated with label molecules and quantification of fluorescent or color intensity.

Thus the invention allows a rapid quantification of global DNA methylation to be achieved. The invention is based on the finding that nucleic acid binding substances coated on the plastic surface can more rapidly and conveniently enhance DNA immobilization and retention on the plastic surface in a simple dry-capture manner at appropriate temperature. The invention is also based on the finding that the immunodetection of 5-methylcytosine can be quantitatively achieved through specific antibody recognition followed by color or fluorescence development and measurement. Therefore the method presented in this invention significantly overcomes the weaknesses existing in the prior technologies and enables global DNA methylation to be quantified rapidly and efficiently.

DETAILED DESCRIPTION OF THE INVENTION

Figure 1:
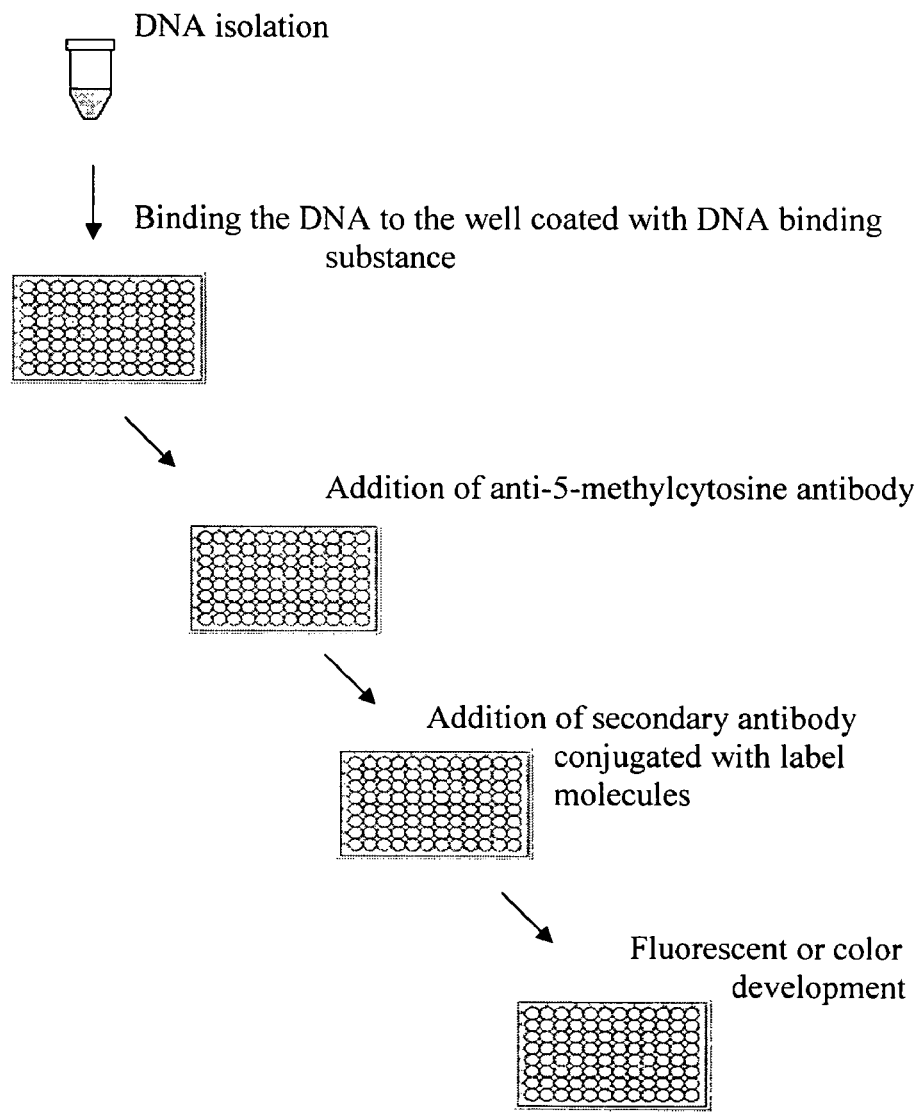
FIG. 1 shows a diagram of the rapid process for quantifying global DNA methylation. The process involves: (1) coating of plastic carrier with nucleic acid binding substance; (2) immobilization of DNA by dry-capture on the glass or plastic well which is coated with nucleic acid binding substance; (3) detection of 5-methylcytosine structure contained in the DNA with the anti-5-methylcytosine specific antibody; (4) detection of anti-5-methylcytosine antibody with the secondary antibody conjugated with label molecules; and (5) fluorescent or color development of antibody conjugated label molecules and quantification of fluorescent or color intensity.

The present invention provides a method and kit for rapidly quantifying global DNA methylation through immobilizing DNA by simple dry-capturing on the plastic carrier followed by immunodetection of 5-methylcytosine structure that is the marker of DNA methylation. A basic outline of the method presented in this invention is described in FIG. 1. This method is particularly useful for rapidly completing a global DNA methylation assay in a short time. This method is also particularly useful for quantifying global DNA methylation in a high throughput format.

According to the method of this invention, DNA could be isolated by lysis of cells with lysis buffer containing a sodium salt, tris-HCl, EDTA, and detergents such as sodium dodecyl sulphate (SDS) or cetyltrimethylammonium bromide (CATB). Tissue fragments should be homogenized before lysing. For example, disaggregating of tissue fragments can be performed by stroking 10-50 times, depending on tissue type, with a Dounce homogenizer. DNA can be further purified by mixing with a high concentration of sodium chloride and then adding into a column pre-inserted with a silica gel, a silica membrane, or a silica filter. The DNA that binds to the silica matrix is washed by adding a washing buffer and eluted with TE buffer or water. DNA can also be isolated and purified by using commercially available DNA extraction kits such as QiaAmp blood or tissue kits. The starting materials for DNA extraction can be from various species including, but not limited to, fresh tissues, frozen tissues, formalin fixed and paraffin embedded tissues, body fluids, and cultured cells.

The purified DNA can be then immobilized on the plastic carrier which is coated with nucleic acid binding substance. The carrier should be polystyrene plastic with high hydrophobic properties and could be in various sizes and forms including, but not limited to, 8-well strip, 12-well strip, 16-well strip, 32-well strip, 48-well strip or microplate, 96-well microplate, 384-well microplate, 1516-well microplate, microscopic slide, and microarray slide. A nucleic acid binding substance can be selected from the epoxy silane, carbodiumide, dicyclohexylcarbodiimide, N-hydroxysuccinimide, p-nitrophenol and poly-L-lysine. Preferably, poly-L-lysine is used for coating the plastic carrier. Coating of the substance can yield a dense layer of amine groups for initial ionic attachment of the negatively charged phosphate groups in the DNA backbone. The DNA can subsequently be attached covalently to the carrier. A 0.01% poly-L-lysine solution is prepared by diluting 0.1% of poly-L-lysine solution (Sigma) with water and PBS at the 1:10 ratios. For multi-well microplate or strips, 150 µl of 0.01% poly-L-lysine solution is added into the well and incubated at room temperature for 2 h. After washing with water, microplate or strips can be dried at 37° C. For the plastic slide, 200 ml of 0.01% poly-L-lysine solution is poured into glass slide box and the slide is then put in the box to soak at room temperature for 1 h. Excess liquid from the slide is removed by spinning the rack of the slide on microtiter plate carriers at 300-500 rpm. The slide is then dried at 40° C. for 20-30 min.

The plastic carrier coated with poly-L-lysine should be stored at least 14 days to become highly hydrophobic and then can be used for DNA immobilization. For multi-well microplate or strip, Purified DNA is diluted with water or TE buffer at different concentrations and 10-50 µl of DNA solution is added into the well of the poly-L-lysine-coated multi-well microplate or strip. Preferably, 25-30 µl of DNA solution is added into the well to just cover the bottom of the well. The multi-well microplate or strip is incubated at 37° C. with no humidity for 2 h followed by incubating at 60° C. for 20 min to evaporate the solution and dry the well. Preferably, the multi-well microplate or strip is incubated at 42° C. with no humidity for 1 h followed by incubating at 60° C. for 30 min to accelerate dry of the well. For microscopic or microarray slide, 0.2-4 ul of DNA solution, depending on the required number of spots, is added to each spot area. The slide can be incubated at 37° C. with no humidity for 30 min followed by incubation at 60° C. for 5 min or incubation at 42° C. with no humidity for 30 min to dry the spotted area. DNA amount to be immobilized can be from 10 to 200 ng, preferably, from 50 to 100 ng, more preferably, 200 ng. A 200 ng of DNA amount would ensure the small fraction of methylated DNA containing in DNA to be detectable while still allowing high specificity to be achieved.

According to the method of the invention, the antibody specific to the 5-methylcytosine is added and reacted with the 5-methylcytosine contained in DNA immobilized on the plastic carrier. Before this step, DNA-immobilized plastic carrier should be blocked with blocking buffer containing 1-3% BSA and phosphate salts. The blocking would prevent the unspecific binding of antibody and thus reduce the background of final detection. The blocking can be done by adding 2% BSA solution into the well of multi-well microplate or strip, or by soaking the slide in the 2% BSA solution at room temperature or 37° C. for 1-2 h. The plastic carrier is then washed with the washing buffer comprising tris-saline and 0.05% tween-20, preferably comprising phosphate saline and 0.1% tween-20. Once the washing is completed, the 5-methylcytosine antibody is added to the plastic carrier. The antibody specific to the 5-methylcytosine may include mouse monoclonal IgG, rat monoclonal IgG, rabbit polyclonal IgG, goat polyclonal IgG and sheep polyclonal IgG. According to the method of this invention, mouse monoclonal IgG is preferable to use. The antibody can be unconjugated or conjugated with biotin, or enzymatic label molecules such as HRP and AP, or fluorescent label molecules such as cy3, cy5, FITC, or gold label molecules, or quantum dot label molecules. The final concentration of the antibody added to the plastic carrier should be 0.5-1 µg/ml. The plastic carrier is incubated at room temperature for 1 h or 37° C. for 45 min after adding antibody. After incubation, the plastic is washed with wash phosphate-saline containing 0.1% tween-20 for 3 times. If the conjugated antibody is used, a colorimetric or fluorescent development can be directly carried out followed by signal measurement. If the unconjugated antibody is used, a secondary anti-mouse, or anti-rabbit, or anti-goat or anti-sheep antibody conjugated with label molecules is added to the plastic carrier. The final concentration of secondary antibody can be from 0.01 µg/mil to 0.5 ug/ml. The label molecules, depending on the requirement of assay, include but are not limited to horse radish peroxidase (HRP), alkaline phosphotase (AP), biotin, fluorescein (FITC), Cy3, Cy5, rhodamine, dynabeads, texas red, Alexa fluor, BODIPY, captivate ferrofluid, cascade blue, beta-lactamase, marine blue, nanogold, Oregon green, pacific blue, and quantum dot. After washing with phosphate-saline buffer containing 0.1% Tween-20, the methylated DNA can be quantitatively detected through the colorimetric or fluorescent development. For colorimetric development, the solution containing color-forming substrates is added to react with enzymatic label molecules such as HRP or AP to yield blue solution or deposit. Other suitable color-forming substrates will be apparent to persons skilled in the art. For fluorescent measurement, fluorescent intensity is directly directed with fluorescent spectrophotometer, fluorescent scanner, or fluorescent microscope.

In an assay, fully methylated DNA at 5-cytosine site by DNA methylase such as M.Sss 1 or NY-2A virus DNA which contains about 50% of 5-methylcytosine can be used as the positive control. The water or TE solution containing no DNA can be served as a negative control.

According to the invention, all of the components for DNA isolation, purification, coating substance of plastic carrier, substances for DNA immobilization, and detection antibodies are commercially available This invention also provides a kit containing all components required for rapid quantification of global DNA methylation in a multi-well microplate/strip format. The kit includes: (a) an mouse monoclonal antibody specific for 5-methylcytosine structure and an anti-mouse antibody conjugated with HRP; (b) a microwell strip or microwell plate coated with poly-L-lysine for DNA immobilization; (c) the concentrated washing buffer comprised of phosphate-saline and surfactants; (d) a colorimetric development solution containing color-forming substrate specific for HRP; (e) a positive control; and (h) an instruction for conducting an assay according to the method of this invention. In one embodiment, the kit further comprises of selected components to meet the requirements for using different measurement equipments.

It has been discovered that the use of the method of this invention is able to drastically reduce the cost and time required for quantifying global DNA methylation. It has been also discovered that the use of the method of this invention is able to allow global DNA quantification to be much easier and more convenient than currently used methods, as the method based on this invention can be carried out with regular equipment such as a microplate reader or microscope. It has been further discovered that the use of the method of this invention enables the quantification of global DNA methylation to be performed in a high throughput format and can be completed with excellent reproducibility.

The method of this invention for quantifying global DNA methylation is further illustrated in the following examples:

EXAMPLE 1

Figure 2:
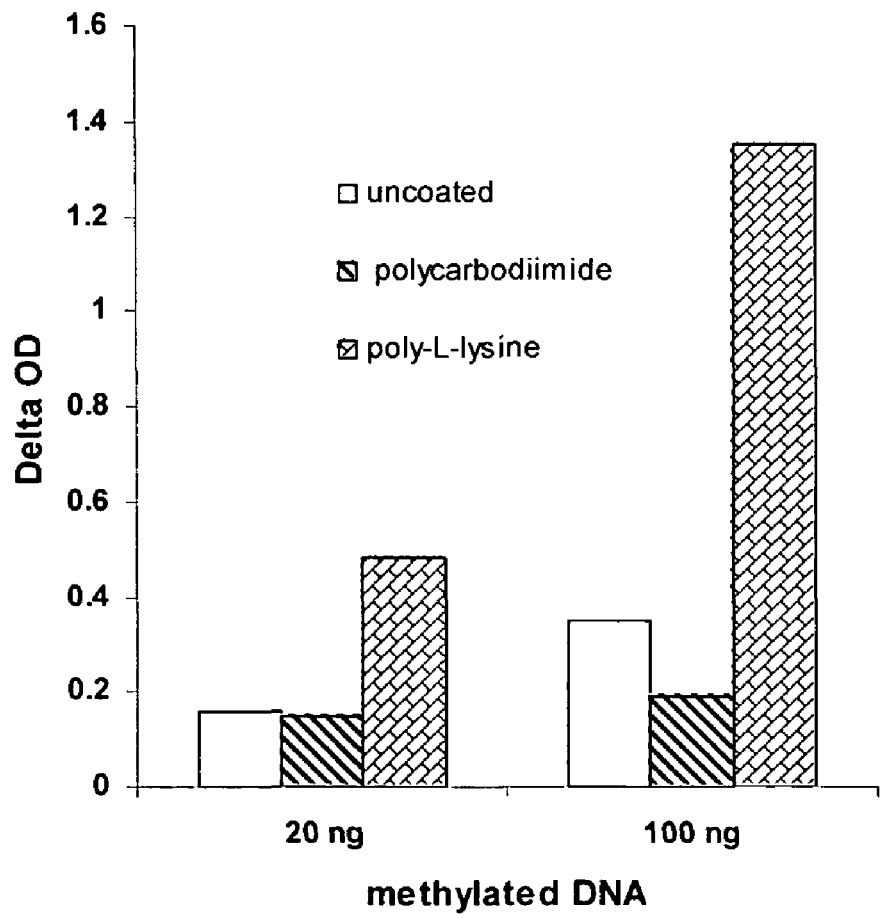
FIG. 2 shows the effect of different nuclei acid binding substances on detection of global DNA methylation. The experiment was carried out as described in Example 1.

The experiment was carried out to compare the effect of different nuclei acid binding substance coating on the detection of global DNA methylation. Polystyrene 8-well strips were coated with 0.01% poly-L-lysine, or 1% polycarbodiimide, respectively. Alter storage at 4° C. for 2 weeks, the coated and uncoated strips were used for DNA immobilization. 30 µl of naturally methylated NY-2A virus DNA at different concentrations were added into the strip wells. The strips were then incubated at 37° C. for 1.5 h followed by incubation at 60° C. for 30 min to dry the wells. The wells were blocked with 2% BSA solution at 37° C. for 30 min followed by washing 3 times. 50 µl of monoclonal anti-5-methylcytosine antibody was then added at 0.5 µg/ml and incubated at room temperature for 1 h. The wells were washed 3 times with PBS containing 0.1% tween-20 after the antibody solution was removed. 50 µl of anti-mouse antibody conjugated with HRP at 0.1 µg/ml was added into the wells and incubated at room temperature for 30 min. The wells were washed 4 times with PBS containing 0.1% tween-20 after the antibody solution was removed. 100 µl of the color development solution containing TMB was added into the wells and wells were observed for 2-10 min for blue color appearance. The 1 M HCl or $H_2SO4$ solution was added to stop the color development and the optical density was measured with a microplate reader. As shown in the FIG. 2, the highest OD values at each concentration point were observed for poly-L-lysine coated wells.

EXAMPLE 2

Figure 3:
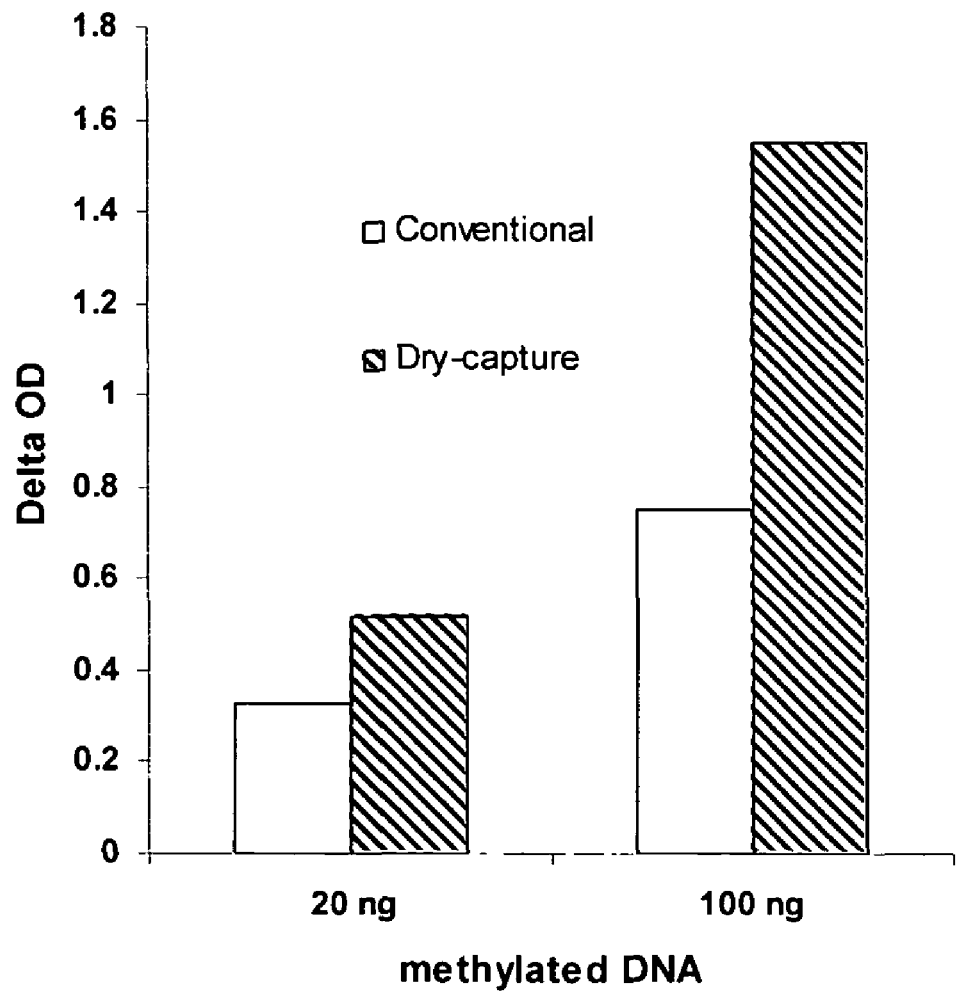
FIG. 3 shows effect of different buffer on detection of global DNA methylation. The experiment was carried out as described in Example 2.
Figure 4:
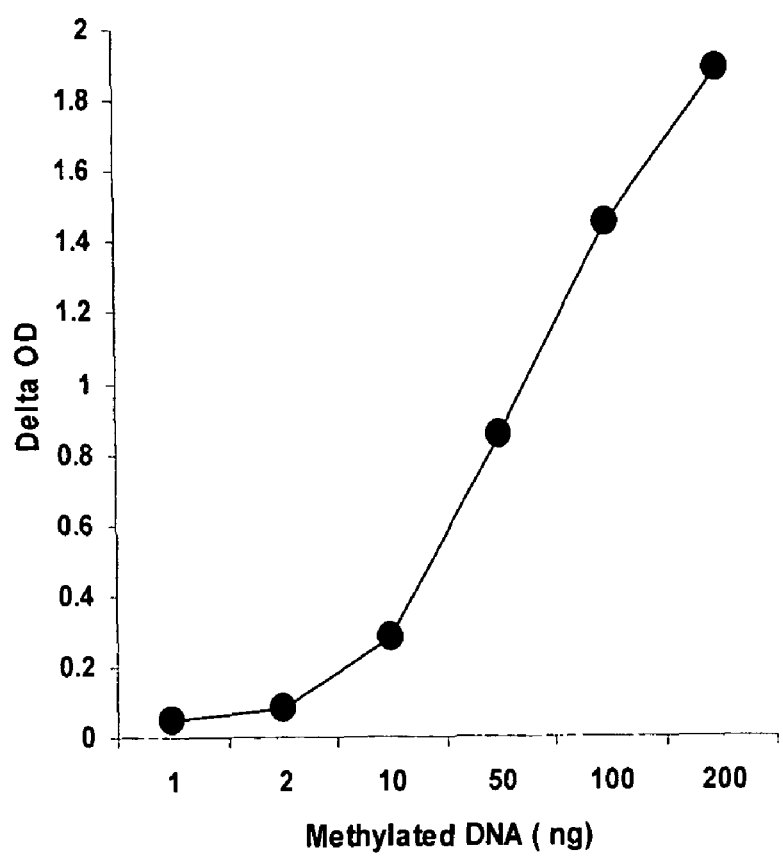
FIG. 4 shows the dry-capture more efficiently increase detection of global DNA methylation. The experiment was carried out as described in Example 3.
Figure 5:
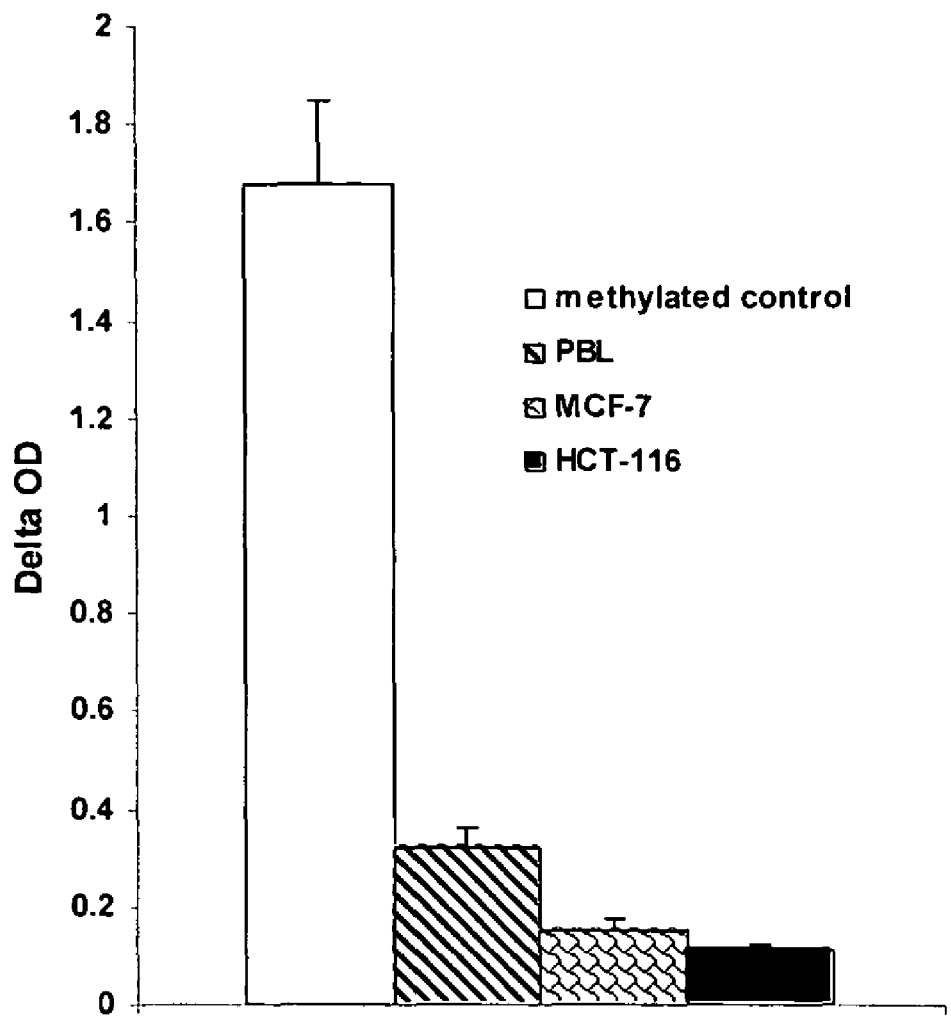
FIG. 5 shows the quantification of global DNA methylation in normal and cancer cells. The experiment was carried out as described in Example 4.

The experiment was carried out to compare the effect of dry-capture method and conventional immobilization methods on the detection of global DNA methylation. Polystyrene 8-well strips were coated with 0.01% poly-L-lysine. After storage at 4° C. for 2 weeks, the coated strips were used for DNA immobilization. With the method of this invention, naturally methylated NY-2A virus DNA was diluted with 1×TE buffer. 30 µl of diluted virus DNA at different concentrations were added into the strip wells. The strips were then incubated at 37° C. for 1.5 h followed by incubation at 60° C. for 30 min to dry the wells. With the conventional method, 50 µl of diluted virus DNA at different concentrations were added into the wells and incubated at room temperature for 4 h or at 4° C. overnight. The remaining solution was removed after incubation. The DNA-immobilized wells with both methods were blocked with 2% BSA solution at 37° C. for 30 min followed by washing 3 times. 50 µl of monoclonal anti-5-methylcytosine antibody was then added at 0.5 µg/ml and incubated at room temperature for 1 h. The wells were washed 3 times with PBS containing 0.1% tween-20 after the antibody solution was removed. 50 µl of anti-mouse antibody conjugated with HRP at 0.1 µg/ml was added into the wells and incubated at room temperature for 30 min. The wells were washed 4 times with PBS containing 0.1% tween-20 after the antibody solution was removed. 100 µl of the color development solution containing TMB was added into the wells and wells were observed for 2-10 min for blue color appearance. The 1 M HCl or $H_2SO4$ solution was added to stop the color development and the optical density was measured with a microplate reader. As shown in FIG. 3, the higher OD values at each concentration point were observed for the wells in which DNA was immobilized by dry-capture method than those by conventional methods.

EXAMPLE 3

The experiment was carried out to examine the detection sensitivity of the method based on this invention on the quantification of global DNA methylation. Polystyrene 8-well strips were coated with 0.01% poly-L-lysine. After storage at 4° C. for 2 weeks, the coated strips were used for DNA immobilization. Naturally methylated NY-2A virus DNA was diluted with 1×TE buffer to different concentrations. 30 µl of diluted virus DNA were added into the wells at the amounts of 2 ng-100 ng/well. The strips were then incubated at 37° C. for 1.5 h followed by incubation at 60° C. for 30 min to dry the wells. The wells were then blocked with 2% BSA solution at 37° C. for 30 min followed by washing 3 times. 50 µl of monoclonal anti-5-methylcytosine antibody was then added at 0.5 µg/ml and incubated at room temperature for 1 h. The wells were washed 3 times with PBS containing 0.1% tween-20 after the antibody solution was removed. 50 μl of anti-mouse antibody conjugated with HRP at 0.1 μg/ml was added into the wells and incubated at room temperature for 30 min. The wells were washed 4 times with PBS containing 0.1% tween-20 after the antibody solution was removed. 100 μl of the color development solution containing TMB was added into the wells and wells were observed for 2-10 min for blue color appearance. The 1 M HCl or $H_2SO_4$ solution was added to stop the color development and the optical density was measured with a microplate reader. The OD values could be observed for the wells which contain as low as 1 ng of methylated DNA.

EXAMPLE 4

The experiment was carried out to examine the effect of the method based on this invention on the quantification of global DNA methylation in normal and cancer cells. Polystyrene 8-well strips were coated with 0.01% poly-L-lysine. After storage at 4° C. for 2 weeks, the coated strips were used for DNA immobilization. Genomic DNA isolated from MCF-7 and HCT-116 cancer cells and from peripheral blood lymphocytes (PBL) was diluted to 8 μg/ml and 25 μl (200 ng) of each genomic DNA were added into the strip wells. The strips were then incubated at 37° C. for 1.5 h followed by incubation at 60° C. for 30 min to dry the wells. An equal amount (200 ng) of naturally methylated virus DNA was used as the positive control. The wells were then blocked with 2% BSA solution at 37° C. for 30 min followed by washing 3 times. 50 μl of monoclonal anti-5-methylcytosine antibody was then added at 0.5 μg/ml and incubated at room temperature for 1 h. The wells were washed 3 times with PBS containing 0.1% tween-20 after the antibody solution was removed. 50 μl of anti-mouse antibody conjugated with HRP at 0.1 μg/ml was added into the wells and incubated at room temperature for 30 min. The wells were washed 4 times with PBS containing 0.1% tween-20 after the antibody solution was removed. 100 μl of the color development solution containing TMB was added into the wells and wells were observed for 2-10 min for blue color appearance. The 1 M HCl or $H_2SO_4$ solution was added to stop the color development and the optical density was measured with a microplate reader. The higher O.D values for PBL DNA were observed.

What is claimed is:

1. A method of rapidly quantifying global DNA methylation comprising:
    a) immobilization of a DNA sample with a binding buffer onto a plastic carrier coated with poly-L-lysine at concentration of 0.001-0.1% b) incubating said sample by two-phase temperature for an appropriate period; wherein said two-phase temperature incubation is to first incubate said sample at 25-42° C. followed by incubating said sample at 50-75° C. and c) immunodetection of 5-methylcytosine structure contained in the DNA sample, wherein the presence of the 5-methylcytosine is indicative of the global DNA methylation.

2. The method according to claim 1 wherein said two-phase temperature incubation is first to incubate samples at 37° C. and followed by incubating samples at 60° C.

3. The method according to claim 1 wherein said an appropriate period is from 2 to 4 hours.

* * * * *